United States Patent
Zingaretti et al.

(10) Patent No.: US 8,951,266 B2
(45) Date of Patent: Feb. 10, 2015

(54) METHODS AND SYSTEMS FOR MODIFYING A PARAMETER OF AN AUTOMATED PROCEDURE

(75) Inventors: Gabriele Zingaretti, Aptos, CA (US); Mohan Bodduluri, Palo Alto, CA (US); Miguel G. Canales, Los Altos, CA (US); Brian E. Tippett, San Antonio, TX (US)

(73) Assignee: Restoration Robotics, Inc., San Jose, CA (US)

( * ) Notice: Subject to any disclaimer, the term of this patent is extended or adjusted under 35 U.S.C. 154(b) by 725 days.

(21) Appl. No.: 13/161,396

(22) Filed: Jun. 15, 2011

(65) Prior Publication Data

US 2012/0179189 A1 Jul. 12, 2012

Related U.S. Application Data

(60) Provisional application No. 61/430,864, filed on Jan. 7, 2011.

(51) Int. Cl.
| | | |
|---|---|---|
| A61B 17/50 | (2006.01) | |
| G06T 7/00 | (2006.01) | |
| A61B 19/00 | (2006.01) | |
| A61B 17/00 | (2006.01) | |

(52) U.S. Cl.
CPC ........... *G06T 7/0004* (2013.01); *A61B 19/2203* (2013.01); *A61B 2017/00752* (2013.01); *A61B 19/5225* (2013.01)
USPC ........................................ 606/133

(58) Field of Classification Search
USPC ........................................ 606/131, 133, 187
See application file for complete search history.

(56) References Cited

U.S. PATENT DOCUMENTS

| | | | |
|---|---|---|---|
| 4,431,007 | A | 2/1984 | Amazeen et al. |
| 6,585,746 | B2 | 7/2003 | Gildenberg |
| 6,676,654 | B1 | 1/2004 | Ball-Petersen et al. |
| 7,107,090 | B2 | 9/2006 | Salisbury, Jr. et al. |
| 7,611,452 | B2 | 11/2009 | Allison et al. |

(Continued)

FOREIGN PATENT DOCUMENTS

| | | |
|---|---|---|
| JP | 2002-541973 | 11/2000 |
| JP | 2010-279714 | 12/2010 |

(Continued)

OTHER PUBLICATIONS

English Translation of Office Action mailed Dec. 10, 2013,, in connection with commonly assigned, Japanese Patent Application No. 2013-547733, Restoration Robotics, Inc., (5 pages).

(Continued)

*Primary Examiner* — Ashley Fishback
(74) *Attorney, Agent, or Firm* — Sharon Upham; Lena I. Vinitskaya (57) ABSTRACT

A variety of systems and methods are described which enable quantitative information to be extracted regarding automated procedures, including those performed at a high speed that may require a user input, without having to interrupt the procedure. In addition, these systems and methods serve to provide information on one or more parameters of the automated procedure, whereby they may be modified, if required, to improve the automated procedure or the results from such a procedure. The systems and methods provided are especially useful in automated hair transplantation procedures.

37 Claims, 4 Drawing Sheets

(56) References Cited

U.S. PATENT DOCUMENTS

| | | |
|---|---|---|
| 2001/0034530 A1 | 10/2001 | Malackowski et al. |
| 2004/0152972 A1 | 8/2004 | Hunter |
| 2005/0096515 A1 | 5/2005 | Geng |
| 2007/0106306 A1 | 5/2007 | Bodduluri et al. |
| 2007/0106633 A1 | 5/2007 | Reiner |
| 2007/0127795 A1 | 6/2007 | Lau et al. |
| 2007/0167801 A1 | 7/2007 | Webler et al. |
| 2007/0171365 A1 | 7/2007 | Tuan |
| 2008/0064953 A1 | 3/2008 | Falco et al. |
| 2009/0306498 A1 | 12/2009 | Bodduluri et al. |
| 2010/0025336 A1 | 2/2010 | Carter et al. |
| 2010/0082039 A1 | 4/2010 | Mohr et al. |
| 2010/0169815 A1 | 7/2010 | Zhao et al. |
| 2010/0249777 A1 | 9/2010 | Sherman et al. |
| 2010/0256479 A1 | 10/2010 | Park et al. |
| 2010/0256504 A1 | 10/2010 | Moreau-Gaudry et al. |
| 2011/0060321 A1 | 3/2011 | Chandler et al. |
| 2011/0105898 A1 | 5/2011 | Guthart et al. |
| 2011/0116703 A1 | 5/2011 | Fu et al. |
| 2011/0160589 A1 | 6/2011 | Fu et al. |

FOREIGN PATENT DOCUMENTS

| | | |
|---|---|---|
| WO | 00/64379 | 11/2000 |
| WO | 2005009215 | 2/2005 |
| WO | 2007/041267 | 4/2007 |
| WO | 2010104718 | 9/2010 |

OTHER PUBLICATIONS

European Search Report and European Search Opinion, in connection with commonly assigned European Patent Application No. 12732235.2, EPO Forms 1507S, 1503, P0459 and 1703, dated Sep. 6, 2013., (5 pages).

PCT International Search Report and Written Opinion for PCT/US2012/020549 of the International Search Authority, Applicant Restoration Robotics, Forms PCT/ISA/210, 220 and 237, mailed Jul. 27, 2012 (15 pages).

English Translation of Office Action mailed Dec. 17, 2013, in connection with commonly assigned Korean Patent Application No. 10-2013-7017818, Restoration Robotics Inc. (2 pages).

Office Action Mailed Aug. 25, 2014, in connection with commonly assigned Canadian Patent Application No. 2,821,343, Restoration Robotics, Inc. (4 pages).

Office Action mailed Jul. 7, 2014, in connection with commonly assigned Australian Patent Application No. 2012204163, (3 pages).

English Translation of Office Action mailed Jul. 1, 2014, in connection with commonly assigned Japanese Patent Application No. 2013-547733 (2 pages).

METHODS AND SYSTEMS FOR MODIFYING A PARAMETER OF AN AUTOMATED PROCEDURE

RELATED APPLICATIONS

This application claims priority under 35 U.S.C. 119(e) to U.S. Provisional Application No. 61/430,864 filed Jan. 7, 2011, entitled "Methods and Systems for Modifying a Parameter of an Automated Procedure".

FIELD OF THE INVENTION

The present application relates generally to automated procedures and more particularly to methods and systems for displaying and modifying a parameter of an automated procedure, such as a hair transplantation procedure, using imaging and processing techniques.

BACKGROUND OF THE INVENTION

There are various medical and cosmetic procedures that may be performed now using various degrees of automation often at a high speed, in some instances using hand-held automated tools, in other instances utilizing automated systems that may include robotic arms, for example. In such procedures, in order to ensure that the automated procedures provide the results desired, user input may be required from time to time. These procedures include, for example, automated hair removal using lasers of varying intensities and wavelengths, or tattoo removal using lasers, including lasers of varying intensities and wavelengths, as disclosed for example in the commonly assigned U.S. Patent Publication No. 2008/0247637.

Another such procedure is a hair transplantation procedure. Hair transplantation procedures typically involve harvesting hair grafts from a donor area, for example, the patient's scalp, and implanting them in a recipient or bald area. Automated hair transplantation systems utilizing a robot, including a robotic arm and a hair follicle tool associated with the robotic arm are disclosed, for example, in U.S. Pat. No. 6,585,746 which describes an automated hair transplantation system utilizing a robot, including a robotic arm and a hair follicle introducer associated with the robotic arm. This system can be used to harvest follicular units from a donor area or implant follicular units into a recipient area with computer assistance.

SUMMARY OF THE INVENTION

In accordance with one general aspect, the present application discloses systems and methods that could be used to analyze and modify, if needed, one or more parameters of the automated procedure. In some embodiments, a method for determining a need to modify a parameter of an automated procedure is provided. The method comprises providing and/or displaying a real-time image of a surface having an automated procedure performed thereon and also providing and/or displaying at least one historic snapshot of the surface, the snapshot identifying a parameter of the automated procedure. The method further comprises modifying the same or a different parameter of the automated procedure to improve results of the procedure. For example, the same or a different parameter may be modified if a value of the parameter in the snapshot suggests that a change is required or desirable, for example, the value of the parameter falls outside an acceptable limit or a range, or is otherwise not advantageous. In some embodiments the value of the parameter may be modified or adjusted by a user, in other embodiments, the modification may be performed automatically. The method may comprise providing a modification interface that allows a user to modify one or more parameters of the automated procedure. The above method may be implemented, for example, in a hair harvesting or hair implantation procedure, or in an automated tattoo removal procedure.

According to certain embodiments, a method for modifying a parameter of an automated hair transplantation procedure is provided. The method comprising providing a real-time image of a body surface having an automated hair transplantation procedure performed thereon; providing at least one snapshot of the body surface, the at least one snapshot identifying a parameter associated with hair transplantation; and modifying the identified parameter or a different parameter associated with the hair transplantation if a value of the identified parameter suggests desirability of the modification. For example, with reference to hair harvesting, the identified or the different parameter may be modified to improve hair follicle dissection.

According to another aspect, the present application provides a method for determining a need to modify a parameter of an automated hair transplantation procedure is provided. The method comprising providing a snapshot of a body surface, the snapshot displaying, for example, an indication of a maximum depth or angle of penetration of a hair transplantation tool with respect to the body surface. The method further comprises allowing for comparison of the displayed indication of depth or angle of penetration (or insertion) against an intended value of depth or angle of penetration/insertion and based on the comparison for determination of whether an adjustment of the depth or the angle of insertion is required.

According to a further aspect, the present application provides an apparatus or a system comprising a processor configured or designed to perform one or more of the inventive methods. The system may also comprise a memory adapted to store, at least temporarily, at least one image. In certain embodiments, the system further comprises an interface adapted to receive one or more images, for example, of a body surface from which follicular units are being harvested and/or where hair grafts are being implanted, In certain embodiments, the system may further comprise an image acquisition device, while in other embodiments the system may be a part of a robotic system for hair transplantation.

In still another aspect, the present application provides machine-readable media on which are provided program instructions for performing one or more of inventive processes or methods described herein.

Other and further objects, features and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Features and advantages of the present invention will become appreciated as the same become better understood with reference to the specification, claims, and appended drawings wherein:

DETAILED DESCRIPTION OF THE PREFERRED EMBODIMENTS

In the following Detailed Description, reference is made to the accompanying drawings that show by way of illustration some examples of embodiments in which the invention may be practiced. It is to be understood that other embodiments may be utilized and structural or logical changes may be made without departing from the scope of the present invention. The following description, therefore, is not to be taken in a limiting sense, and the scope of the present invention is defined by the appended claims.

The term "tool", "harvesting tool" or "implantation tool", as used herein in reference to hair transplantation, refers to any number of tools or end effectors that are capable of dissecting, harvesting or implanting follicular units ("FUs") from a body surface. Such tools may have many different forms and configurations. In many embodiments, the tool comprises a hollow tubular shaft and thus may be labeled, for example, a cannula, a needle, or a punch. The distal ends of such tools (for example, punches, coring devices, cutting and/or trimming devices, needles), are typically sharpened, to various degrees, to assist in harvesting or implanting the follicular unit. Other tools applicable for alternative procedures that could benefit from the inventions of the present application may comprise, for example, lasers, or tattoo removal tools.

Embodiments of the methods of the present invention may be implemented using computer software, firmware or hardware. Various programming languages and operating systems may be used to implement the inventions described herein.

It should be understood that various inventive concepts described herein may be applied to a variety of procedures and applications. For convenience of description, the following description will be discussed by example in reference to hair transplantation procedures. Hair transplantation procedures that are carried out using automated (including robotic) systems or computer-controlled systems have been described, for example, in the commonly assigned Publication No. US 2007/0106306, which is incorporated herein by reference. Robotic hair transplantation systems generally require accurate positioning of a tool under robotic control. When implementing a semi-automated or a fully automated procedure it is likely that modification to certain hair transplantation parameters may be required. According to one aspect disclosed herein, the present application provides methodology enabling modifications to be made to the value of parameters, for example parameters associated with the hair transplantation procedure, such that the modifications may be made easily, and without necessarily interrupting the procedure itself.

One of the benefits of an automated hair transplantation system is to substantially reduce the time of the procedure while performing hundreds of repetitive and tedious steps associated with hair harvesting and/or hair implantation procedures. One of the consequences of using an automated hair transplantation system, however, is that the speed at which the automated hair transplantation process occurs may be too fast for the doctor who directs the automated system to easily observe its operation, discern certain parameters, and make any necessary adjustments of the parameters of harvesting or implantation process. Since skin tension, or hair follicles' density, thickness, and many other parameters may vary from patient to patient, and even within different areas of the scalp of the same patient, the surgeon's input is required, for example, to adjust the depth or the angle of the insertion of the tool, to ensure the transplantation is successful (e.g., the follicular units are harvested without transecting or otherwise damaging them). The automated systems may be operating so quickly that unless the doctor is willing to temporarily halt the procedure, he may not be able to tell if any adjustment to the process is required, before it is too late, and the procedure has been completed or is well under way. With a hair transplantation procedure, in addition to the system requirements and considerations, consideration of various aspects of the patient involved also have to be dealt with. For example, all body surfaces are not as elastic as others, some may be formed of tissue that is easily penetrated by a harvesting tool, whereas other tissue may be more difficult to penetrate, even if a similar force is applied over a similar time period to the surface to puncture the skin. Therefore the need to adjust a parameter of the hair transplant procedure from one patient to another, or from one portion of a donor area to another is to be expected, especially when performed by the automated tools or robotic systems. Should any adjustment be necessary, typically, a certain amount of time is often lost when the automated process is interrupted to check to see if adjustment is necessary, or to actually make the necessary adjustment. If the initial adjustment does not solve the issue, further interruption will also be required until the problem is solved. The utilization of automated systems and methods for hair transplantation, therefore create other issues in their endeavor to improve the speed and efficiency of the automated procedure.

According to the various embodiments described herein, a variety of systems and methods have been developed which enable quantitative information to be extracted regarding the hair transplantation procedure without having to interrupt the procedure. In addition, these systems and methods serve to provide information on one or more parameters of the hair harvesting procedure, whereby they may be modified, if required, to improve the hair harvesting procedure or the results from such a procedure. In one configuration, for example, the system allows the user to visually inspect a magnified image of the harvested hair(s) and based on the inspection, the user may approve or modify one or more parameters to enhance the system's performance, or the results from such a procedure. In another configuration, for example, the system may automatically carry out such "visual" inspection of the "image" of the harvested hair(s) and automatically modify one or more parameters to enhance the system's performance, or the results from such a procedure. The visual inspection may be based on the capture of quantitative parameters of previous harvesting or implantation attempts, such parameters including but not limited to the angle of the tool, the depth of penetration of the tool, the force applied to the tool during penetration, whether the dissected follicular unit was retained in the harvesting tool, whether the follicular unit was transected during the dissection, and/or the rotational speed of the tool. For example, image processing may be utilized to identify whether a follicular unit was retained in the harvesting tool. The system may be configured to take a snapshot at an instance when the tool is retracted from the body surface, and the image processor may be configured or programmed to check an absence of a follicular unit (if there is cavity in the body surface from which the follicular unit was removed), or if the follicular unit is still present to some degree. Based on the finding, the processor may then automatically determine (without input from the user) if any modification to one or more of the associated parameters is required and automatically instruct the required modification accordingly. In this manner, the system is able to automatically carry out a "visual" inspection of the "image" of the harvested hair(s) and automatically modify one or more parameters to enhance the system's performance. The identification of a value associated with various parameters, and the modification thereof; enables the user (or the system), for example, to modify the angle at which the tool is inserted into the body surface, the depth to which it is inserted, the force applied on insertion, the selection of tool size, and/or the rotational speed of the tool, to thereby minimize damage to the follicular unit being removed, and/or improve the quality of the removed specimen, preferably preserving its integrity. These systems and methods may also serve to reduce the transection rate of follicular units during the dissection process. These systems and methods can be incorporated into the use of or as part of an automated or semi-automated system, and/or of part of a computer or robotically controlled system. The modifications identified above can be carried out in a timely manner to avoid continuous operation under the undesirable parameters, and they could be performed without having to interrupt or substantially delay the automated transplantation procedure.

Although the various examples and embodiments described herein will use follicular units or hairs for purposes of describing the various aspect of the invention, it should be apparent that the general understanding of the various concepts discussed can be applied more broadly to other appropriate applications. It should be understood that although the methods described herein are especially suited for use with a robotic system for hair harvesting and/or implanting, they can be applied to other applications. These additional applications may include, for example, an automated tattoo placement or removal, or an automated hair removal.

Figure 1:
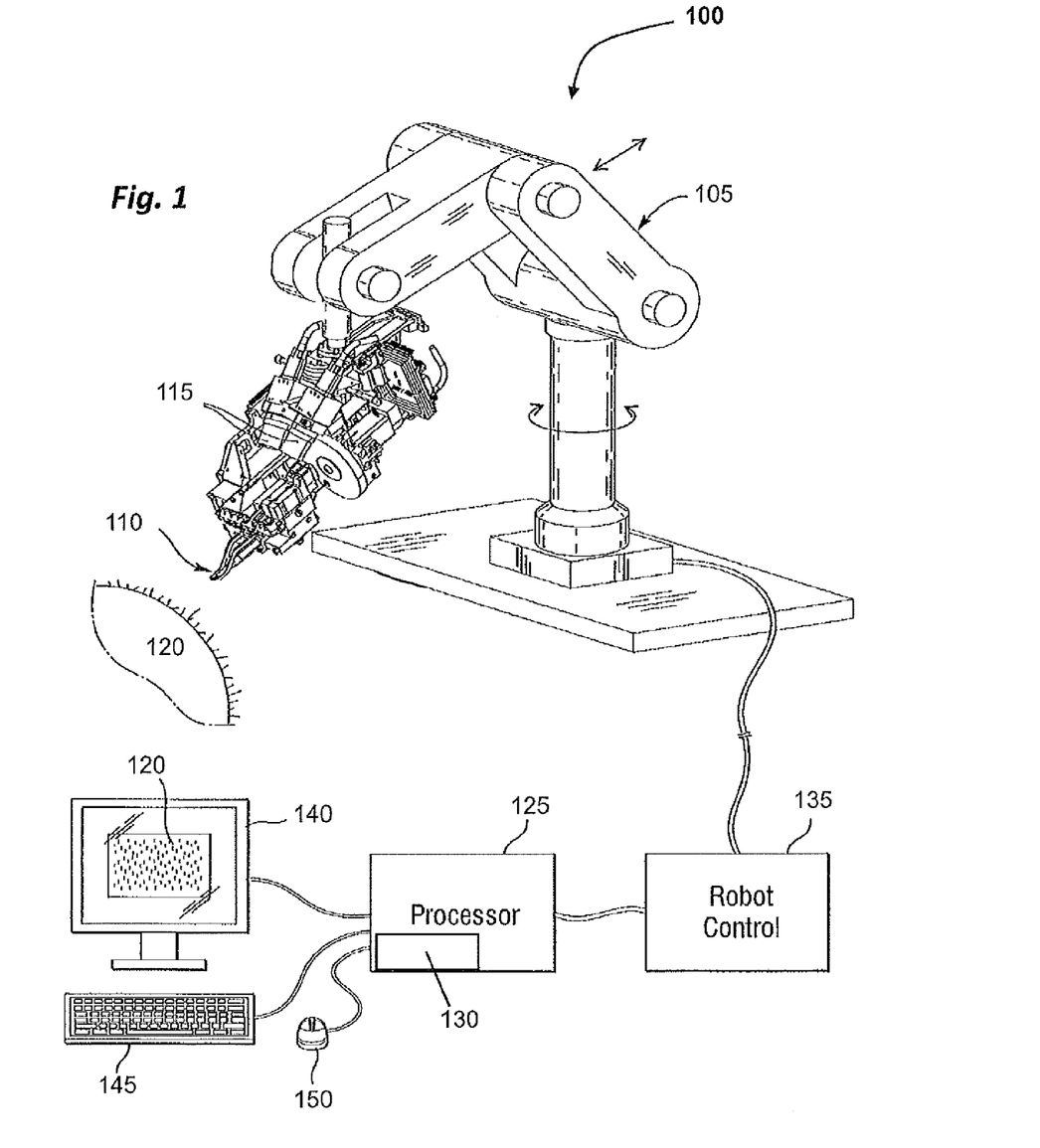
FIG. 1 is a schematic representation of an example of a robotic system that could be implemented in various embodiments of the inventions described herein.

FIG. 1 is a schematic perspective view of an example of a robotic system 100 for harvesting and/or implanting follicular units into a body surface, such as the scalp. The system 100 includes a robotic arm 105 to which is coupled a harvesting or implanting tool 110. Various motors and other movement devices may be incorporated to enable fine movements of an operating tip of the tool 110 in multiple directions. The robotic system 100 further includes at least one (and preferably two for stereo vision) image acquisition device 115 which may be mounted in a fixed position, or coupled (directly or indirectly) to a robotic arm 105 or other controllable motion device. The operating tip of the tool 110 is shown positioned over a body surface 120, in this case a part of the patient scalp having hair follicles thereon.

The processor 125 of FIG. 1 comprises an image processor 130 for processing images obtained from the image acquisition device 115. The image processor 130 may be a separate device or it may be incorporated as a part of the processor 125. The processor 125 may also instruct the various movement devices of the robotic arm 105, including the tool 110, and act, for example, through a controller 135 as schematically shown in FIG. 1. The controller 135 may be operatively coupled to the robotic arm and configured to control the motion of the robotic arm, including the motion based on the images or data acquired by the image acquisition device. Alternatively, controller 135 may be incorporated as a part of the processor 125, so that all processing and controls of all movements of all the tools, the robotic arm and any other moveable parts of the assembly, including those based on the images or data acquired by the image acquisition device, are concentrated in one place. The system 100 may further comprise a monitor 140, keyboard 145, and mouse 150. A magnified image of the body surface 120 can be seen on the imaging display or monitor 140. In addition, the system 100 may comprise other tools, devices and components useful in harvesting, and/or implantation of the hair follicles, or in hair treatment planning. The system further comprises an interface (not shown) adapted to receive an image data, various parts of the system allow an operator to monitor conditions and provide instructions, as needed. The processor 125 may interact with the imaging device 115 via the interface. The interface may include hardware ports, cables, leads, and other data transmission means, or it may comprise a computer program.

Some non-limiting examples of an image acquisition device 115 shown in FIG. 1 include one or more cameras, such as any commercially available cameras. The image acquisition or imaging device may be held, for example, by a robotic arm, or by any other mechanism or means. Of course, various image acquisition devices or a combination of several devices could be used with any of the embodiments of the systems and methods described herein. The image acquisition device 115 may comprise a device that takes still images, it can also comprise a device capable of real time imaging (e.g., webcam capable of continuously streaming real time information), and/or it could also have a video recording capability (such as a camcorder). While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system 125, shown incorporated in the image processor 130 in FIG. 1, to control the imaging operation and process image data.

Typically, the processor 125 operates as a data processing device, for example, it may be incorporated into a computer. The processor 125 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 125 may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor 130 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present invention is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the invention may be, at least partially, implemented on a card for a network device or a general-purpose computing device. The processor/image processor may also include memory, storage devices, and other components generally known in the art and, therefore, they do not need to be described in detail here. The image processor could be used in conjunction with various manual, partially automated and fully automated (including robotic) hair transplantation systems and devices, including but not limited to systems for hair harvesting, or hair transplantation.

The imaging display device 140 may comprise a high resolution computer monitor which may optionally be a touch screen. The imaging display may allow images, such as video or still images, to be readable and for follicular units, and parts thereof, to be visualized. Alternatively, the imaging display device 140 can be other touch sensitive devices, including tablet, pocket PC, and other plasma screens. The touch screen may be used to modify the parameters of the hair transplantation procedure, directly through the image display device.

Methods, apparatus and systems consistent with the invention may be carried out by providing a modification interface, or user modification interface, including clickable icons, selection buttons in a menu, dialog box, or a roll-down window of an interface that may be provided to feed into the computer. According to another embodiment, the imaging display device 140 may display the selection window and a stylus or keyboard for entering a selection, for example, directly on the display itself. According to one embodiment, commands may be input via the modification interface through a programmable stylus, keyboard, mouse, speech processing system, laser pointer, touch screen, tablet computer, personal digital assistant (PDA), a remote input device (such as a pendant), or other input mechanism. The remote input device may include clickable icons, selection buttons, dialog boxes, or roll-down windows which are the same as or similar to those found on the user modification interface, providing a convenient way for the user to control common user interface functions from their position at the patient's side. Alternatively, the remote input device may only accommodate, for example, a subset of such modification controls, making for a more compact pendant. In yet another embodiment, the remote input device may be configured to accommodate additional modification controls. Moreover, either the remote input device or any other input mechanism may have icons which allow the user to control the robotic arm, allowing the user move the robotic arm away from the patient, or incorporate a STOP button, enabling the user to terminate operation of the robotic arm or hair transplantation tool in the event of an emergency. Alternatively, the modification interface may comprise a dedicated piece of hardware. In some embodiments the selections or adjustment made through the modification interface may be executed by code instructions that may be executed on the computer processor.

The program that runs the method and system may include a separate program code including a set of instructions for performing a desired operation or may include a plurality of modules that perform such sub-operations of an operation, or may be part of a single module of a larger program providing the operation. The modular construction facilitates adding, deleting, updating and/or amending the modules therein and/or features within the modules.

The program may include an electronic auditing function that enables capturing of selective data that is part of and contained within the apparatus or system. For example, the captured data may include a value of a parameter associated with the hair transplantation procedure, the apparatus or system carrying out the procedure, and/or the patient. The electronic auditing function may be configured in some embodiments to capture the individual steps or portions thereof that the system performs during the hair harvesting or hair implanting process of hair transplantation. The electronic auditing system may also be configured to capture parameter values associated with the hair transplantation procedure that are ascertained from the processing of the captured individual steps or portions thereof.

The program may receive unique identifier information and/or additional information and may access, for example, a storage device having data associated with the unique identifier information and/or additional information.

In some embodiments, a user may select a particular method or embodiment of this application, and the processor will run a program or algorithm associated with the selected method. For example, a user may select (e.g. by clicking and dragging, or clicking on a user interface icon, or by entering a command, a voice command, etc.) a hair harvesting program which includes operation of both sharp piercing needle and a duller coring needle. Alternatively the user may select to run a program controlling only a coring needle for a period of time to evaluate and adjust (if needed) one or more parameters of operation of a coring needle; or to run a program controlling only an implanting/site making needle to evaluate and adjust, for example, its depth of insertion or an angle.

A controller that may be operatively coupled to the processor may allow the speed, angle, and/or direction of a drive, as just an example, of the robotic tool (e.g., the hair harvesting tool) to be substantially automatically controlled. In certain embodiments, various types of position sensors may be used. For example, in certain embodiment, a non-optical encoder may be used where a voltage level or polarity may be adjusted as a function of encoder signal feedback to achieve a desired angle, speed, or force.

To aid in the understanding of the inventions of the present application, examples of the methodology will be described and explained in reference to the hair harvesting procedure. It will be apparent that the teachings can equally be applied to the hair implantation process, or to other appropriate process with adaptations being made to accommodate the requirements of such process. To this end, before describing the hair harvesting procedure according to an embodiment of the invention, an example of the harvesting tool shall be described briefly to aid in the subsequent discussions.

Hair transplantation tools that can be used in a substantially automated, including robotic, system have been described, for example, in the commonly assigned U.S. Patent Publication No. 2008/0234699. In the case of a single sharp punch or needle being used for harvesting, sometimes if the sharp punch penetrates or punctures too deeply into the body surface, there is an increased chance that the follicular unit will be transected, thereby damaging it or rendering it unusable. Therefore, in some embodiments it may be desirable to use a hair harvesting or hair removal tool that comprises two concentric needles or punches, one of which is used to dissect deeper but is less sharp to decrease the chance of transecting follicular unit. In certain embodiments, an inside needle may be sharp or semi-sharp, and an outside needle may be relatively dull or less sharp than the inside needle. The inside needle may be used to initially pierce the skin and to form an incision, for example, of 0.5 mm to 2.0 mm deep. The outside needle can then follow the inside needle into the incision made by the inside needle and continue through deeper tissue to a depth of, for example, 5-8 mm. The relatively dull edge of the outside needle dissects the follicular unit separating it from the surrounding tissue and guides the follicular unit into the lumen of the outer needle without transecting or otherwise damaging the follicular unit. This enables removal or harvesting of the follicular unit while preserving its integrity. The outer needle body is sized and configured to at least partially surround or encapsulate a follicular unit. One or both of the inner and outer needles may be axially movable relative to one another, one or both of the inner and outer needles may also optionally rotate or oscillate. It is not required, however, for implementation of the inventions described herein that the inner needle be sharp and the outer needle be more dull, and it will be understood that in various embodiments the positions of these needles could be reversed, or various different configurations of the needles may be used, including the use of a single dissecting or harvesting needle (instead of two co-axial needles).

Figure 2A:
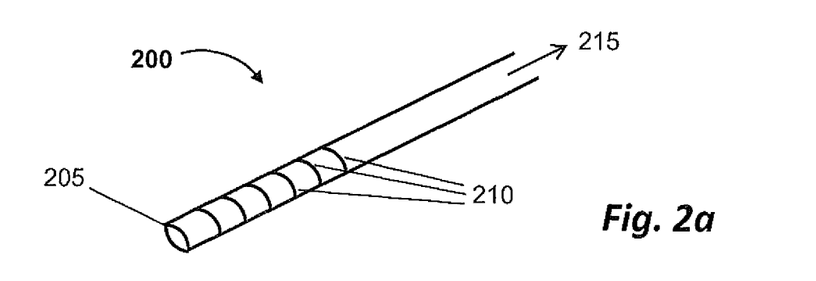
FIGS. 2a and 2b are examples of punches or needles that could be utilized in various embodiments of the inventions described herein.
Figure 2B:
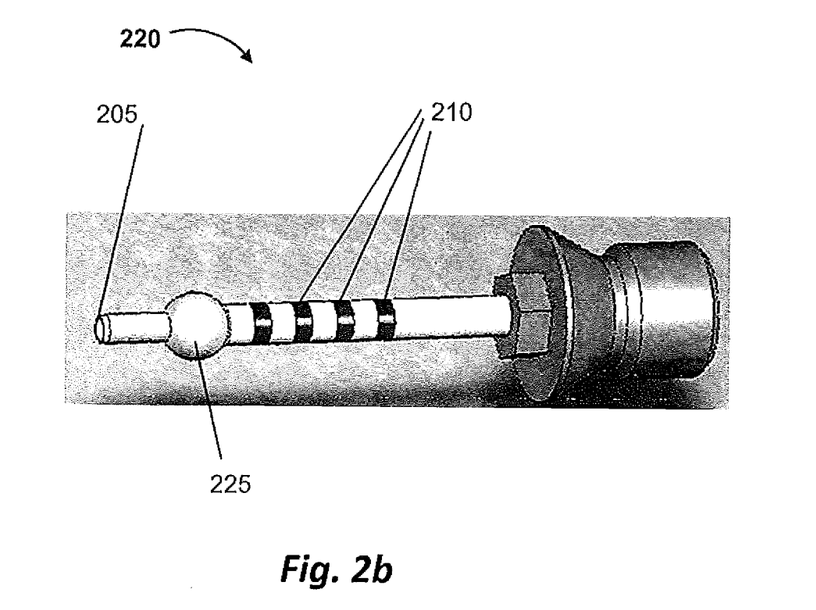

FIG. 2a illustrates an example of a distal portion of the needle or punch 200 that may be used in the harvesting tool. The punch 200 includes an elongated body having a sharp distal tip 205. The term "sharp" distal tip 205 as used herein means that it is sharp enough to pierce or cut a skin or body surface (not shown). The elongated body may be pushed into the skin such that its sharp distal tip cuts or penetrates tissue, or skin layers to a desired depth (e.g. through the epidermis, or upper dermis). A lower portion of the elongated body, the portion closer to the distal tip, may be provided with graduation markings 210 on its outer surface. Such markings assist in identifying the depth of insertion of the punch 200 in the body surface as explained in more detail later in reference to FIG. 3. The punch 220 represents an example of an alternative punch, for example, a dissecting needle that may be used in the embodiments implementing the two-needle configuration of the harvesting tool, or it could be a single needle harvesting tool. Such punch 220 may include markings 210 and may also include a stop 225, as illustrated in FIG. 2(b). The stop 225 is an example of a structure that limits the depth of insertion of the distal end of the punch 220 into the body surface. As the distal tip penetrates the body surface to the desired depth, the graduation markings provide a visual indication of the depth to which the distal tip 205 has entered the body surface. Having dissected the follicular unit from the surrounding tissue, the harvesting tool is withdrawn from the body or skin surface. Depending upon the particular configuration of harvesting tool utilized, the harvesting tool may be removed from the skin while a dissected follicular unit may still remain in the body surface, and then subsequently removed, for example, with the additional assistance of forceps, or vacuum, or other appropriate tools or mechanisms. Other harvesting tools are capable of dissecting the follicular unit and also removing it when the harvesting tool is removed from the skin. For example, a retention member (not shown) may be incorporated into the inner and/or outer needles of the harvesting tool to assist with the removal of the follicular unit.

The proximal end of the tool 200 may be configured to incorporate appropriate sleeves, slidable shafts, or other such structures to move the elongated body or bodies (needles/punches) axially and optionally radially relative to one another. In an alternative embodiment, the proximal end of the tool may be operatively connected to a mechanical system, electromechanical system, a pneumatic system, hydraulic system, or a magnetic system configured to effect controlled movement of the tool 200 (e.g., movement of the inner and outer needles relative to one another), and to facilitate a semi- or fully-automated tool to be employed. In yet another alternative embodiment, either or both of the inner and outer needles may be operatively coupled to a biasing mechanism, such as a spring mechanism, or other such release mechanism to facilitate movement of the needles in the axial direction, in a quick, or slow or otherwise controlled manner.

Figure 3:
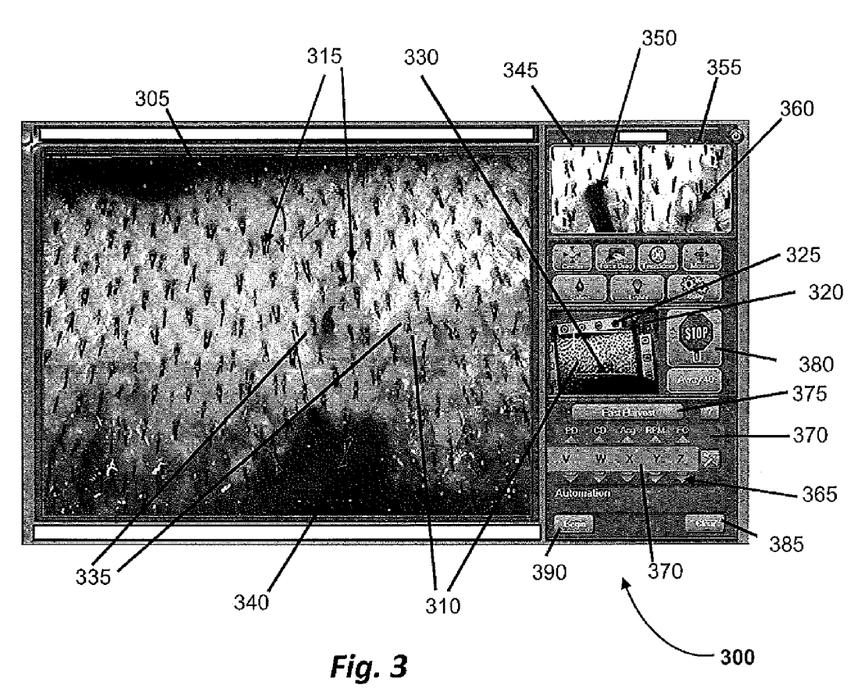
FIG. 3 is an example of a screen shot of a user display, which could be used to implement various embodiments of the invention.

FIG. 3 illustrates the view on an imaging display or monitor 300, which embodies several features of the invention, and facilitates validation or modification of parameters of an automated procedure, in this particular example a hair harvesting procedure. The monitor 300 shows several features, some or all of which may be utilized in various embodiments of the methods described herein, for example, in hair harvesting, hair removal, or hair implantation procedures. The monitor 300 includes a main section, which in the illustrated example takes up about two-thirds of the viewable space, and displays a real time image 305 of a body surface 310 which is undergoing a hair harvesting process. The real time image as used herein means an image that displays real time information captured by an image acquisition device, such as one or more cameras, for example, high-magnification camera(s) (such real time image is intended to include an image displayed, for example, with short delays of approximately up to 250 milliseconds, or in some examples from approximately 20 milliseconds to about 230 milliseconds). Some examples of the devices that could be used to obtain real time image include various cameras (e.g. webcam, surveillance cameras, linear cameras), or ultrasound sensing. In the streaming real time image, the user is able to see the individual follicular units 315 in the immediate area surrounding a currently being harvested (being removed, or being implanted) follicular unit, and operation of the tool as it is being inserted into and withdrawn from the skin. The monitor may also optionally display in addition to this large close up real time view 305, a more global view 320 (for example, using a pair of low-magnification cameras), that may appear on another section of the monitor 300 as a supplemental real-time image as seen in FIG. 3, this view displaying a real time image of the larger, for example, bound area from which the hairs are being harvested in this portion of the procedure. The tool bar of the user interface may allow to select which view or views to display (stereo, high-magnification, or low-magnification, etc.) For convenience of the description, dissecting or harvesting of a single follicular unit (which may comprise one or more hair follicles) will be referred to as a harvesting event, and implanting of a single follicular unit will be referred to as an implantation event. For other procedures where present inventions may be implemented, the relevant event may be, for example, a hair removal event, or a tattoo removal event. Optionally, fiducials or markers 325 shown in the global view 320 can be placed, for example, directly onto the body surface, or may be attached to a skin tensioner that may be used in the hair transplantation procedure or other appropriate procedure where skin tensioning is desired. In this more global view 320, a virtual box 330 is identified, this box corresponding to the region of the body surface that is shown in the real time image 305. In this manner, with the concurrent showing of the main real time image 305 and the global real time view 320, the user is able to obtain an overall view and better understanding of from where follicular units still need to be harvested, from where follicular units have already been harvested, and be generally informed of issues that may be arising as the procedure continues. An example of an issue that might be arising for example, is that the tool may be operating off-center, that is actually centering at a point different to the targeted point of the follicular unit instructed by the processor and/or control unit; or perhaps the user may be noticing an increase in the transection rate of the dissected/harvested follicular units. The apparatus, system and methods of this application, enable the user or the automated apparatus/system itself to utilize the information displayed, such that the parameters of the procedure during at least a portion of the procedure may be validated or modified, if warranted, and that it may be done without having to necessarily interrupt the procedure, or interrupt it for a significant time.

As illustrated in FIG. 3, the visual representation of the real-time information may be combined using known image processing techniques, for example, with a virtual representation 335 of the location from where follicular units have been harvested. Such virtual representation will assist in differentiating the already dissected follicular units, for example, by forming a colored circle or other configuration around dissected/harvested follicular unit to more clearly visually represent that harvesting has occurred in that region. The examples of various virtual representations are described in a commonly assigned provisional application identified by Ser. No. 61/425,571 entitled "Methods and Systems for Directing Movement of a Tool in Hair Transplantation Procedures," and filed on Dec. 21, 2010. The color selection of the above visual representations may be such that these already harvested regions can be more easily differentiated, for example, from the area of blood 340 that also may be seen in the image 305. In other embodiments, for example, the real time image may be combined with a virtual representation of the location from where follicular units have been already implanted.

The streaming real time images 305 are useful in making certain decisions, for example, where a user needs to override an automated selection of the next follicular unit to be harvested that is made by the system. For example, by observing automated operation, the user may want to avoid an area where hair grafts were already harvested or avoid harvesting areas near scars or any other undesirable harvest sites, and therefore, needs to override on the spot a selection made automatically by the system in such area. In other situations, because the automated operation of the tool may be too fast, streaming of real time images may result in an insufficient time for the user to observe certain parameters and timely made an appropriate decision. Therefore, in addition to the main real time image 305 (and optionally the global real time view 320), one or more supplemental snapshots or images, as described below, may be also provided concurrently. In FIG. 3, by way of example two additional supplemental images/snapshots are shown, each of the snapshots taken at a different moment in time during the streaming of the real time images, but relating to the same follicular unit that is being harvested, or the same harvesting event. In other words, such snapshots, even though are based on the real time imaging, are not the real time images, but rather represent historic information of a state of the procedure at a particular moment or interval in time during streaming of the real time images. In this particular example, each of the first supplemental image 345 and the second supplemental image 355 is a still image. However, instead of a still image, in some embodiments snapshots 345 and 355 may be videos, for example, short videos of 0.5 to 3 seconds duration, or it may be simply a recording of the previously taken real time images that is run or looping in a slow motion or pace (e.g. less than 30 frames per second) to allow the user to observe the details and identify whether any adjustments are desired or warranted. The first supplemental image 345 may be captured, for example, when the harvesting needle 350 penetrated or punctured the body surface to a maximum designated depth of penetration and the skin has substantially stabilized, recovered, or settled from the rapid action of the harvesting needle, or at a predetermined time interval after activation of the needle, for example a tenth of a second later. If a punch 200 with graduation markings 210 is utilized, the user will be able to see how deep into the body surface the punch 200 has penetrated in this first supplemental image 345. With the correct magnification, the user will be able to at least see the various markings, and ascertain the approximate length of the inner needle or punch 200 that has penetrated the body surface. Alternatively, an electronic auditing function in the program associated with the harvesting procedure may be configured to capture quantitative information, a value pertaining to the depth of insertion of the punch 200, and perhaps retain that information in memory for later retrieval or use.

The second supplemental image 355 may be captured at an instance when the harvesting event, such as the dissection of a follicular unit, is substantially complete. Typically, it would happen once a distal tip of the harvesting needle has been retracted from the body surface. For example, in the case of a two co-axial needle configuration, the image may be captured at a time when both the inner and outer needles have been retracted from the body surface, or a predetermined time after the second of the two needles is removed. One of the benefits of having this second supplemental image 355 is that the user can observe if, and optionally how, the follicular unit is being elevated from the body surface. For example, if the follicular unit or a portion of it is seen lying on the surface in unusual orientation, it may be an indication that follicular unit was transected during harvesting. On the other hand, if the follicular unit appears to be at least partially elevated from the surface, this may be an indication that dissection was successful, and the follicular unit is now ready to be removed from the body surface, for example, by forceps or some other means. In addition, the user may be able to observe an image 360 of the incision made around the follicular unit, and may be able to ascertain if the harvested follicular unit was centered with respect to image 360 of the incision, or if the harvesting tool operated off-center with respect to the targeted follicular unit. Alternatively, an assessment of the centering of the tool may be accomplished automatically. For example, an electronic auditing function in the program associated with the harvesting procedure, may be configured to capture quantitative information, a value pertaining to the amount that the follicular unit is offset from the center of the image 360, and perhaps retain that information in memory for later retrieval or use.

While the first and second supplemental images 345 and 355 are displayed as essentially historical information pertaining to harvesting of a particular hair follicular unit, the real time image 305 and the more global real time image 320 continue to display real-time imaging of the ongoing follicular unit harvesting process. For each event, that is for each follicular unit harvesting attempt, a supplemental image set (that may comprise simply one supplemental snapshot, such as image 345, or any desirable number of the supplemental snapshot images, for example 3, 4, or 5 snapshots) may be captured. In the example of FIG. 3, for each follicular unit harvest attempt, a first supplemental image 345 and a second supplemental image 355 is captured, providing a record of information pertaining to the depth the punch needle 200 penetrated the body surface, the angle of the needle, and also the quality of the harvested follicular unit and/or the quality of the harvesting procedure.

When viewing the first supplemental image 345, should the user recognize a deviation from expectation or desire, for example, should it be identified that the depth of penetration is too deep, the user has the opportunity to reduce the penetration depth. If the penetration depth is too deep, the incision may cut through the epidermis and dermis into the subcutaneous fat. A typical pattern of damage to the hair follicle that may result from the penetration depth of the punch 200 being too deep is a transection in the upper portion of the hair follicle. Should the user become aware of this problem, he may, for example, by using his mouse to click on an arrow 365 on the panel 370, which is associated with the penetration or puncture depth (PD) of the punch 200. Once the user clicks this arrow 365, the value V associated with the puncture depth (PD) is modified, and the program of the computer is able to execute that instruction, communicating that modification to the controller such that the puncture depth PD of the punch 200 is modified. Depending upon the time it takes for the program to carry out this modification request (or based on a specific setting of the delay in implementing the modification), the next follicular unit harvest attempt may be carried out at this modified penetration or puncture depth PD, or alternatively, the modified puncture depth PD may be applied to a subsequent attempt. Likewise, if the user should recognize or identify that the depth of penetration or puncture is too shallow, he may choose to increase the penetration depth utilizing the appropriately programmed arrow on the panel 370, which will similarly provide the necessary instructions to the control unit such that the penetration depth is increased. In some embodiments, instead of the arrow on the panel 370, the user may use a corresponding arrow or button of the remote control input device. In this manner, the user is given the opportunity to modify the value of a parameter if it is found to be not optimal, less desirable, or outside one or more acceptable limits, during a session of an automated hair transplantation procedure, without having to necessarily stop the harvesting procedure. It will be appreciated that although it may not perhaps be necessary to stop the harvesting procedure, it may be desirable from either the user's perspective and/or the system's perspective (depending upon the nature of the program and the related software and hardware configuration(s)), that the system be at least paused so that user has a longer opportunity to view the first supplemental image 345 and/or to make the necessary change(s) to the system. Once the modification has been carried out, the user may then re-start the procedure, enabling the modification to be executed. The user will have the opportunity to view a first supplemental image 345 associated with the modified penetration or puncture depth, and ensure that the modification was sufficient for his/her purposes. If not, further modification can be requested in a similar manner. Alternatively, the imaging processing may be utilized to automatically identify whether a modification of puncture depth is required. For example, the system may be configured to take a snapshot or first supplemental image 345 at an instant indicative of the maximum penetration depth after the skin has settled. The image processor may be configured to automatically identify (without input from the user) the markings on the punch, and to identify where the body surface is with respect to the markings. Such identification may be based on captured data, and not on an actual "visual image". For example, if it has been predetermined that there should be three markings on the punch that are visible above the skin surface, but only two such marking are identified by the image processing, based on these findings, the processor may be configured or programmed to automatically modify the puncture depth accordingly. It could be modified, for example, to ensure that subsequent punching of the body surface by the harvesting tool results in three markings being seen in a future supplemental image, such as image 345. In the above example, the processor may automatically reduce the penetration/puncture depth by an amount substantially equivalent to the spacing between the second and third markings or as otherwise necessary to ensure the desired result (in this case visibility of the three markings) is attained. In this manner, the system is able to automatically carry out a "visual" inspection of the "image" and automatically modify one or more parameters (in this instance is the depth of penetration) to enhance the system's performance.

Similar modification can be carried out pertaining to other parameters associated with the hair harvesting procedure. Also, by analyzing the status of one parameter, it may be determined that some other parameter of the procedure should be modified. For example, as indicated in FIG. 3, the value W of the coring depth (CD) can be modified, modifying for example the depth to which the coring needle penetrates the body surface, the depth used to dissect the follicular unit from its surrounding tissue. A coring depth range of, for example, between 8 mm and 9 mm is common to achieve the desired dissection level of the subcutaneous fat. If the coring depth setting is set too high, a typical pattern of damage is a transection in the lower portion of the hair follicle. On the other hand, the coring depth may be set too low. In this situation this value may be modified, for example, if the second supplemental image 355 indicates that the "harvested" follicular unit is not being sufficiently elevated after the harvesting attempt. Therefore, by analyzing one parameter, such as the elevation of the follicular unit, it may be desirable to modify another parameter, such as the coring depth (CD) of the harvesting tool. The value X of the angle of the harvesting tool can be modified as well. This value may be modified, for example, if the second supplemental image 355 indicates that the attempts to harvest follicular units are transecting the follicular units. The value Y associated with the speed at which the harvesting tool rotates, RPM, may be modified, for example, if the second supplemental image indicates that the body surface is being torn. The value Z associated with the force at which the harvesting tool is forced into the body surface to penetrate the skin may also be modified in a similar manner. Rather than or in addition to modifying the value of Z, however, the user may utilize the information he has acquired to modify the tensioning of the skin surface rather than the force. That is, he or she may take the opportunity to alter the amount of tension applied by a skin tensioning device (if such device is used), or perhaps employ an alternative skin tensioning device. It will be apparent therefore that the modification need not necessarily directly relate to the identified parameter but indirectly do so, such that the modification enhances the results of the harvesting procedure. In some instances, modification of one parameter, may also affect the value of another parameter. Modification of the force applied to the punch is one such example since modifying the skin tension in response to discerning information from the supplemental images may cause better penetration, and hence have the potential to alter the actual resulting depth of penetration. Moreover, the value of the parameter being analyzed or the parameter to be modified does not need to be displayed.

In the event that the value Z of the force FC, at which the harvesting tool is forced to penetrate or advance through the layers of skin to dissect tissue, is modified to increase the force applied, yet no increase in coring depth CD results, using the parameters displayed, or otherwise determined or calculated, the user can make a decision (or the system may suggest a decision) to perhaps, rather than try increasing the value of the force FC again, to select another harvesting tool, perhaps one with a larger diameter punch, or a punch of different parameters.

The above-described example illustrates a harvesting tool comprising two harvesting needles (a sharper piercing punch and a coring/dissecting punch). The methods described herein, however, can equally apply to a single-needle harvesting tool. In this configuration of the harvesting tool the user display may provide a selection for a single punch, such as needle 200. Such selection is shown by example as 375 in FIG. 3. If a punch similar to the punch 200 with graduation markings 210 was utilized, using a snapshot like a first supplemental image 345 would allow a user to ascertain how deep into the body surface the punch 200 was penetrating. Should the user determine that the depth of penetration was too deep, the user may choose to reduce the penetration depth by, for example, using a mouse to click on an arrow (365) on the panel 370, which is associated with the penetration or puncture depth (PD) of the punch 200. Once the user clicks this arrow 365, the value V associated with the penetration depth (PD) is modified, and the program is able to execute that instruction, communicating that modification to the controller such that the penetration depth PD of the punch 200 is modified.

Various other features may be incorporated onto the user display, to facilitate the successful automated transplantation of hair while ensuring safety and control of the system to the user. For example, a STOP feature 380 may be incorporated, enabling the user to stop the hair transplantation procedure being carried out at any step within the procedure, though it will be appreciated that the system may be programmed to stop in certain instances, for example, at a point when the needle is retracted from the patient's body surface. Also, all parameters entered in the system may be cleared by clicking on the "clear" icon 385 before entering a new set of parameters. To begin the hair transplantation procedure one may select icon 390. It can be seen from FIG. 3, that the system may include many other control icons, none, some or all of which may be utilized in any one procedure.

In some embodiments, the memory of the system may only allow a predetermined number of image sets to be stored (at least temporarily or permanently) for later retrieval or use, or may allow all, or a subset of all harvest attempts to be stored. In another embodiment, using the mouse, the user may click an icon on the display to recall the last five, for example, image sets, thus visualizing the last five harvest attempts which may be displayed to the user, and parameters associated with the quality of the hair transplantation system or the procedure. In another aspect, the computer program may be configured to not only retrieve the images stored, but to list the values of the parameters associated with the hair harvesting process.

Figure 4:
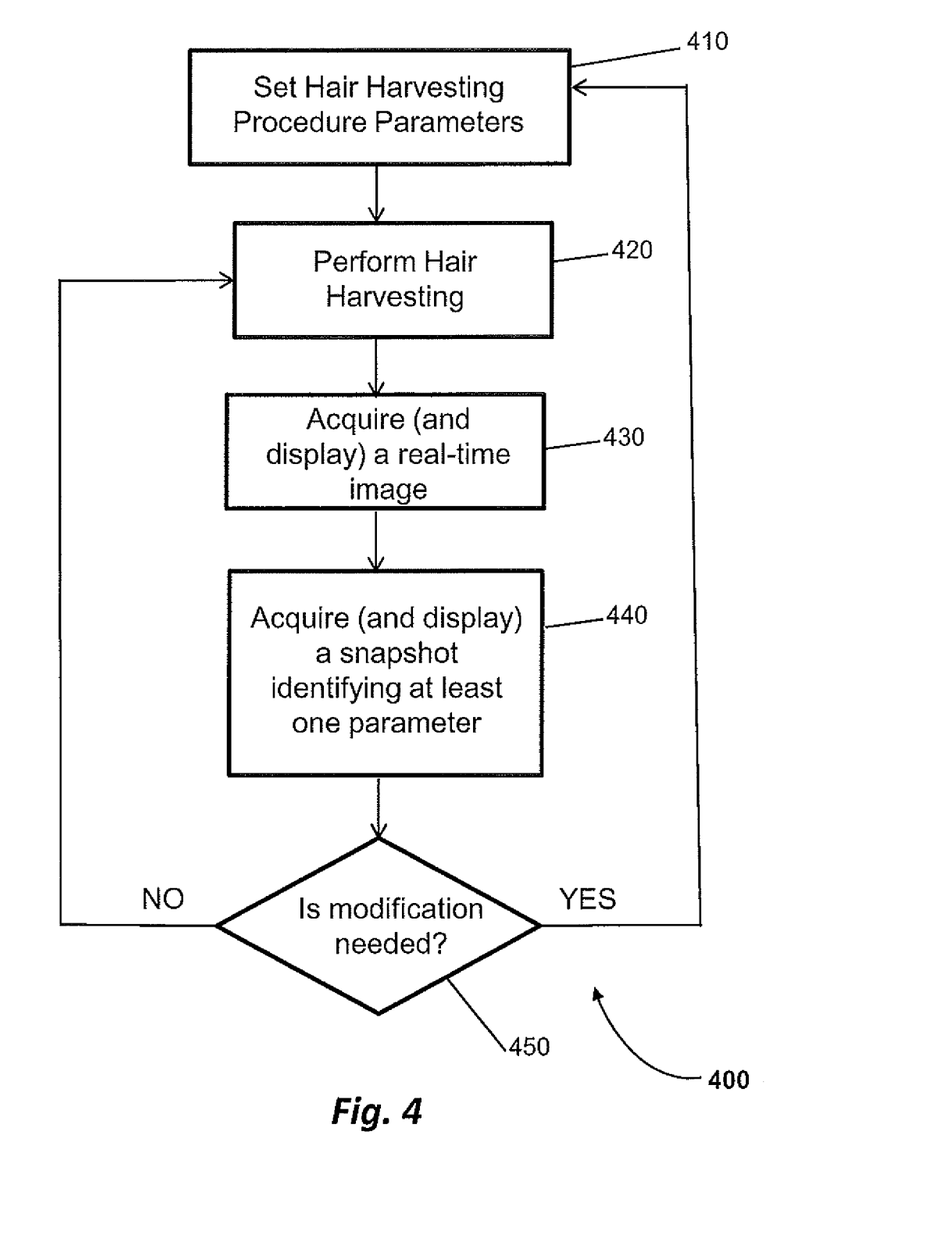
FIG. 4 is a block diagram illustrating an example of a general methodology according to one aspect of the invention.

FIG. 4 is a block diagram illustrating an example of a general methodology 400 employed by the present invention, as applied to hair harvesting example, though it will be apparent that the steps can equally be applied to the hair implantation procedure, or other appropriate procedure, with the necessary modifications. First, at step 410, before the hair harvesting procedure begins, parameters for the hair harvesting procedure may be selected, the parameters may include, but are not limited to, the force that is to be applied to the punch needle, the revolutions per minute associated with the punch needle, the depth of penetration of the punch needle, the revolutions per minute associated with the dissection needle, and the depth of penetration of the dissection needle. These parameters may be selected by the user, or the system may suggest a set of parameters from the memory, for example, based on the demographic patient data. Having selected these initial parameters, the automated hair harvesting procedure begins in step 420 by performing one or more hair harvesting attempts or events. As procedure is being performed, a real time image of the procedure may be acquired and may be displayed, as shown in step 430. It will be appreciated that in some embodiments due to a substantial automation it may not be required to show the real time image to the user, so the display aspect of this step may be optional, although it is anticipated that a real time image will be a useful feature to provide to the user, even if it is not required for the operational function of the automated system. As previously explained and described, in addition to the real-time image, in step 440 one or more supplemental images or historic snapshots may be acquired and displayed for some or all individual hair harvesting events. The timing of the supplemental snapshots is dictated by the parameter or the parameters of the hair harvesting procedure the value of which the snapshot is intended to ascertain, for example, the time of penetration of the skin by the harvesting punch. Again, in certain embodiments where modifications are made automatically by the system, displaying the snapshots to the user is not required for the operational function of the automated system, but it is still a useful feature for allowing the user to override the automatic selection. If it is determined in step 450 that no modification of any parameter of the hair harvesting procedure is needed, the harvesting procedure continues for one or more hair harvesting events. However, if it is determined in step 450 that at least one parameter associated with the hair harvesting procedure needs to be modified to improve the results of the procedure, whether the modification is by the user or an automated modification, the method returns to step 410, where the modification to the value of the hair harvesting parameter is made, prior to performing the next hair harvesting event in step 420. As indicated earlier, depending on a desired setting or upon the speed of this methodology, even though a value of a parameter may be modified in step 410, it may not necessarily affect the hair harvesting procedure performed on the next hair that is attempted to be harvested, but will affect a certain subsequent hair. It should be noted that by identifying in the snapshot the state of one parameter of the hair harvesting process, it may be determined that this and/or some other parameter should be modified, as described above in reference to FIG. 3.

According to one general aspect of the present application, a method for determining a need to modify a parameter of an automated procedure is provided. The method comprises providing and/or displaying a real-time image of a surface having an automated procedure performed thereon and also providing and/or displaying at least one historic snapshot of the surface, the snapshot identifying or allowing to ascertain/determine a parameter of the automated procedure. The method further comprises modifying the same or a different parameter of the automated procedure to improve the results of such procedure, for example, if a value of the parameter in the snapshot is outside one or more acceptable limits or otherwise less desirable. In some embodiments the value of the parameter may be modified or adjusted with a user input, in other embodiments, the modification may be performed automatically. For example, the processor may register the value of the parameter and compare it to a predetermined or selected acceptable value. If the difference is above a predetermined maximum threshold value, below a predetermined minimum threshold value, or falls outside a predetermined specified range of values, the processor may determine an adjustment to be necessary, and automatically apply the necessary modification to the parameter or another appropriate parameter. The method may comprise providing a modification interface that allows a user to modify one or more parameters of the automated procedure. Various examples of the parameters of interest have been described in reference to various procedures. For example, in reference to hair transplantation modification of parameter(s) may be directed to improving dissection of the follicular units. The parameters of interest may comprise a depth of insertion of the harvesting needle, or the angle of insertion, or centering of the needle relative to the follicular unit, or the force or rotational speed of the needle movement, or ability of the needle to dissect and at least partially elevate the follicular unit from the skin surface. In reference to removing color tattoos, such parameter of interest may be, for example, a laser wavelength and/or intensity. In some applications of the method, the automated procedure is an automated tattoo removal procedure and the modification interface allows the user to modify the intensity or wavelength of a light source. In other applications of the method, the automated procedure is an automated hair removal procedure and the modification interface allows the user to modify the intensity or wavelength of a light source.

According to another aspect, a method for determining a need to modify a parameter of an automated hair transplantation procedure is provided. The method comprising providing a snapshot of a body surface, the snapshot displaying, for example, an indication of a maximum depth or angle of penetration or insertion of a hair transplantation tool with respect to the body surface. The method further comprises allowing for comparison of the displayed indication of depth or angle of insertion against an intended value of depth or angle of insertion and based on the comparison for determination of whether an adjustment of the depth or the angle of penetration is required. In some embodiments the determination is carried out automatically by a processor, the processor being part of an automated system. In other embodiments, determination is accomplished with a user input through a modification interface. The method may further comprise providing a second snapshot of the body surface, the second snapshot taken when a distal end of the tool is retracted from the body surface; and based on the second snapshot, determining if a hair transplantation event meets an intended hair transplantation criteria. In some embodiments the criteria may be a centering of the hair transplantation tool with respect to a follicular unit. Centering of the hair transplantation tool with respect to a follicular unit typically reduces the chances of damaging the dissected hair. To determine whether the intended hair transplantation criteria (e.g. centering) is met, one may compare an actual value indicative of the centering or a value associated with the centering of the hair transplantation tool with respect to the follicular unit, with an intended or desired value of the centering of the hair transplantation tool with respect to the follicular unit. In other embodiments the criteria may be no transection of the dissected follicular unit. In yet other embodiments the criteria may be an elevation of a follicular unit from the body surface, and determination comprises comparing a parameter indicative of the elevation of a follicular unit from the body surface with an intended value of the elevation of a follicular unit from the body surface. Once a determination has been made that the hair transplantation criteria has not been met (typically falling outside one or more acceptable or desirable limits), a parameter that influences the criteria can be modified such that the resulting dissection of the follicular unit is improved. For example, if it found that follicular units are not being sufficiently elevated from the body surface (that is, the elevation criteria is not being met), the puncture depth may be modified (for example, by increasing it), such that subsequent elevation depths meet the desired criteria, alternatively the force at which the harvesting punch penetrates the body surface can be increased or decreased as desired. It will be apparent to the reader that there are may be more than one parameter or combination of parameters that can be modified to influence hair transplantation criteria.

It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be performed in a partially or substantially automated fashion, including performed using robotic systems.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention.

The processor for use in the present invention may comprise any suitable device programmed and configured to perform various methods described in detail in the present application, including methods directed to modifying a parameter of a hair harvesting or implanting procedure to improve results of the procedure, for example, if the same or other identified parameter associated with the procedure is unacceptable. In some embodiments modification may be accomplished through the modification interface. For example, the processor for use in the present invention may be a processor comprising a set of instructions for executing operations, the set of instructions including instructions for processing one or more images of a body surface to identify and/or display a parameter (or a plurality of parameters) associated with, for example, the hair transplantation procedure, and for modifying or allowing to modify such parameter (or other parameters) as may be necessary or desirable to successfully carry out the procedure. The system for use according to the inventions described herein may comprise in addition to a processor an image acquisition device. For example, a system for determining a need to modify a parameter of an automated hair transplantation procedure may be provided. The system may comprise a user interface including a processor, the processor configured to process a snapshot of a body surface which provides an indication of a depth or angle of penetration of a hair transplantation tool with respect to the body surface, and to allow for comparison of the indicated depth or angle of penetration against an intended value of the depth or the angle of penetration.

In some embodiments, the system may comprise a user input device, the user input device configured to allow a user to interactively modify the depth or angle of penetration of the hair transplantation tool based on the comparison. In other embodiments, the processor is configured to automatically modify the depth or angle of penetration of a hair transplantation tool based on the comparison, for example, to bring the future depth of penetration or the angle of the tool within a predetermined deviation from the intended value.

Certain embodiments relate to a machine-readable medium (e.g., computer readable media) or computer program products that include program instructions and/or data (including data structures) for performing various computer-implemented operations. A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. I may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

The various embodiments described above are provided by way of illustration only and should not be construed to limit the claimed invention. Those skilled in the art will readily recognize various modifications and changes that may be made to the disclosed embodiments without departing from the scope of the claimed invention. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to the fields described by example in the present application. The description, therefore, is not to be taken in a limiting sense, and the scope of the present invention is defined by the appended claims.

It will be further appreciated by those skilled in the art that the invention is not limited to the use of a particular system, and that various automated (including robotic), or partially or semi-automated systems and apparatus may be used for positioning and actuating the respective removal tools and other devices and components disclosed herein.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. Applicant regards the subject matter of the invention to include all novel and nonobvious combinations and subcombinations of the various elements, features, functions, and/or properties disclosed herein.

What is claimed is:

1. A method for determining a need to modify a parameter of operation of a system comprising a tool for use with an automated hair transplantation procedure, the method comprising:

providing at least one historic snapshot of the body surface based on a real-time image, the at least one historic snapshot identifying a parameter associated with hair transplantation, wherein the identified parameter relates to at least one of the following: 1) whether a follicular unit was transected during hair transplantation, 2) a force which is applied to the tool, or 3) elevation of a follicular unit from the body surface during the hair transplantation;

determining if a value of the identified parameter associated with hair transplantation is outside one or more acceptable or desirable limits; and modifying at least one parameter of operation of the tool if a value of the identified parameter associated with hair transplantation is outside one or more acceptable or desirable limits.

2. The method of claim 1, wherein modifying is accomplished with a user input through a modification interface.

3. The method of claim 2, wherein the user modification interface comprises a keyboard, a mouth, a voice or speech recognition device, a laser pointer, touch screen, tablet computer, personal digital assistant (PDA), or a remote user input device.

4. The method of claim 1, wherein modifying is accomplished substantially automatically, the method further comprising registering the value of the identified parameter and comparing the registered value to a predetermined value, and if the difference between the registered value and the predetermined value is outside an acceptable range, determining an adjustment to be automatically applied.

5. The method of claim 1, wherein the identified parameter cannot be easily discerned by the user in the real time image.

6. The method of claim 1, wherein the identified parameter is associated with the quality of the hair transplantation procedure.

7. The method of claim 1, wherein the identified parameter comprises a depth or an angle that a hair transplantation tool penetrates the body surface.

8. The method of claim 1, wherein the identified parameter comprises an absence of the follicular unit or indicates a cavity in the body surface from which the follicular unit was removed.

9. The method of claim 1, wherein the at least one snapshot comprises a snapshot of a previous harvesting or implantation attempt.

10. The method of claim 1, wherein the hair transplantation procedure comprises a hair harvesting procedure and modifying the identified parameter improves dissection of follicular units.

11. The method of claim 1, wherein the hair transplantation procedure comprises a hair implantation procedure.

12. The method of claim 1, comprising at least two snapshots, the first of the at least two snapshots comprising an image acquired at a first instance during an automated hair transplantation event, and the second of the at least two snapshots comprising an image acquired at a second instance during the automated hair transplantation event.

13. The method of claim 12, wherein the first instance is associated with a skin being stabilized after a hair transplantation tool has penetrated the body surface to a maximum depth of penetration.

14. The method of claim 12, wherein the second instance is associated with substantial completion of the hair transplantation event.

15. The method of claim 12, wherein the at least two snapshots is an image set, and the image set is taken for some or all hair transplantation events, and wherein the method further comprises storing a number of the image sets in a storage device, and displaying at least one of the number of the image sets.

16. The method of claim 15, wherein displaying the at least one of the number of the image sets comprises displaying it to the user concurrently with displaying the real time image of a current hair transplantation event.

17. The method of claim 1, further comprising selecting a hair transplantation tool based on the identified parameter.

18. The method of claim 1, wherein determining the value of the identified parameter is based on captured data.

19. The method of claim 1, wherein modifying the at least one parameter affects not a next follicular unit on which the tool operates, but a subsequent follicular unit on which the tool operates.

20. The method of claim 1, further comprising concurrently providing a real time image in addition to the at least one historic snapshot.

21. A method for determining a need to modify a parameter of operation of an apparatus for use in an automated hair transplantation procedure, the method comprising:
providing a real-time image of a body surface where the apparatus is used to perform an automated hair transplantation procedure;
providing at least one historic snapshot of the body surface, the at least one historic snapshot allowing to identify whether a criteria associated with hair transplantation is met, wherein the criteria relates to at least one of the following: 1) whether a follicular unit was transected during hair transplantation, 2) a force which is applied to the hair transplantation tool, or 3) elevation of a follicular unit from the body surface during the hair transplantation; and
modifying at least one parameter of operation of the apparatus if the criteria is not met, modification of the at least one parameter of operation of the apparatus influencing the criteria.

22. The method of claim 21, comprising determining and/or displaying a value associated with the criteria.

23. The method of claim 21, further comprising modifying the tension in the body surface.

24. The method of claim 21, wherein provision of the at least one snapshot comprises acquiring data at an instant in time.

25. The method of claim 21, wherein identifying a criteria comprises visual identification.

26. The method of claim 21, comprising at least two snapshots, the first of the at least two snapshots comprising an image acquired at a first instance during an automated hair transplantation event, and the second of the at least two snapshots comprising an image acquired at a second instance during the automated hair transplantation event.

27. The method of claim 21, further comprising providing at least another snapshot of the body surface allowing to identify the influenced criteria.

28. The method of claim 21, wherein modifying is accomplished substantially automatically, the method further comprising registering a value of the criteria and comparing the registered value to a predetermined value, and if the difference between the registered value and the predetermined value is outside an acceptable range, determining the at least one parameter to modify, and automatically modifying the determined the at least one parameter.

29. The method of claim 21, wherein modifying at least one parameter of operation comprises selecting another tool, or a tool of different parameters.

30. A method for modifying a parameter of operation of a tool for use with an automated hair transplantation procedure, the method comprising:
providing at least two historic snapshots of a body surface based on a real-time image, the at least two historic snapshots identifying a parameter associated with hair transplantation, the first of the at least two historic snapshots comprising an image acquired at a first instance associated with a skin being stabilized after a tool has penetrated the body surface to a maximum depth of penetration and the second of the at least two historic snapshots comprising an image acquired at a second instance associated with substantial completion of the hair transplantation event; and
modifying at least one parameter of operation of the tool if a value of the identified parameter associated with hair transplantation is outside one or more predetermined limits.

31. The method of claim 30, further comprising verifying whether the follicular unit was removed from the body surface and wherein the modification step comprises automatically determining if any modification is required.

32. The method of claim 30, wherein modifying the at least one parameter is carried out with a use of one or more of the following: a touch screen, a stylus, keyboard, mouse, dialog box, a roll-down window, speech processing system, tablet computer, a remote input device, or substantially automatically by execution of programmable instructions.

33. The method of claim 30, wherein determination of whether modification is required is performed automatically and further comprising allowing a user to override such automatic modification.

34. The method of claim 30, wherein the first or the second instance comprises a predetermined time interval after activation of the tool.

35. The method of claim 30, wherein the second instance comprises when a distal tip of the tool has been retracted from the body surface.

36. A method for determining a need to modify a parameter of operation of a system comprising a tool for use with an automated hair transplantation procedure, the method comprising:
providing at least one historic snapshot of the body surface, the at least one historic snapshot identifying a parameter associated with hair transplantation, wherein the identified parameter relates to a centering of the tool about a follicular unit to be harvested or implanted;
determining if a value of the identified parameter associated with the centering of the tool about a previously harvested or implanted follicular unit is outside one or more acceptable or desirable limits; and
modifying at least one parameter of operation of the tool for harvesting or implanting subsequent follicular unit if the value of the identified parameter associated with centering of the tool about the previously harvested or implanted follicular unit is outside one or more acceptable or desirable limits.

37. The method of claim 36, wherein the identified parameter comprises quantitative information pertaining to the amount the center of the harvested or implanted follicular unit is offset from a center of the tool.

* * * * *